United States Patent [19]

Sölter

[11] Patent Number: 4,965,451

[45] Date of Patent: Oct. 23, 1990

[54] METHOD AND APPARATUS FOR THE CONTACTLESS TESTING OF THE SURFACE AND INNER STRUCTURE OF A SOLID WORKPIECE

[76] Inventor: Hans-Joachim Sölter, Schumanstrasse 44b, 2822 Schwanewede, Fed. Rep. of Germany

[21] Appl. No.: 366,741

[22] Filed: Jun. 14, 1989

[30] Foreign Application Priority Data

Jun. 21, 1988 [DE] Fed. Rep. of Germany ....... 3820862

[51] Int. Cl.$^5$ .................... G01N 21/00; G01N 21/63
[52] U.S. Cl. .................................. 250/330; 250/332; 250/334; 250/341
[58] Field of Search ................ 250/330, 332, 334, 341

[56] References Cited

U.S. PATENT DOCUMENTS

| | | |
|---|---|---|
| 4,328,516 | 5/1982 | Colpack et al. ............... 250/330 X |
| 4,520,504 | 5/1985 | Walker et al. ................. 250/334 X |
| 4,594,508 | 6/1986 | Runciman ....................... 250/334 |
| 4,647,220 | 3/1987 | Adams et al. ................... 250/330 X |

*Primary Examiner*—Constantine Hannaher
*Assistant Examiner*—Jacob M. Eisenberg
*Attorney, Agent, or Firm*—Collard, Roe & Galgano

[57] ABSTRACT

A method and apparatus is provided to effect the contactless testing of the surface and inner structure of a solid workpiece, wherein a single pulse of an electromagnetic exciting beam, preferably of a focused beam, is projected against the workpiece and the effect of the locally and temporarily induced workpiece temperature, measured as generated infra-red radiation, is processed, providing information concerning the surface and inner structure of the workpiece. The single pulsee of the laser beam is broken up into a multiplicity of component beams whose images, simultaneously projected upon the workpiece, are combined in a field or line by means of which the workpiece is analyzed.

14 Claims, 3 Drawing Sheets

METHOD AND APPARATUS FOR THE CONTACTLESS TESTING OF THE SURFACE AND INNER STRUCTURE OF A SOLID WORKPIECE

The present invention relates to a method and apparatus to effect the contactless testing of the surface and inner structure of a solid workpiece or test sample, whereby a single pulse of an electromagnetic exciting beam, preferably of a focused laser beam, is projected against the workpiece and the effect of the locally and temporarily induced temperature, measured as workpiece generated infra-red radiation, is processed, providing information concerning the surface and inner structure of the workpiece.

According to the *Journal of Applied Physics,* Vol. 32, No. 9, September, 1961, pp. 1679–1684, a method is disclosed whereby a test sample can be heated by means of a single pulse of a laser beam of a predetermined intensity and temporary duration. The heat generated on the surface of the test sample during irradiation thereof is absorbed into the test sample. As a result of thermal conductivity, an increase in temperature occurs on the surface of the test sample opposite the irradiated surface. This increase in temperature is measured by means of a sensor and is used to determine the thermal conductivity of the test sample.

Apart from providing for determination of thermal conductivity, the above referenced article offers no impetus for determining any additional information concerning the nature of the surface and the inner structure of the solid test sample. Such information, however, is precisely the kind need to be able to perform, for example, contactless testing for quality control purposes, for example, in industrial manufacturing processes. A testing procedure is only suitable for application in quality control when it ensures that the time required to perform each testing procedure does not exceed an acceptable order of magnitude. Orders of magnitude in the range of several minutes is not acceptable, especially for utilization in assembly line processes. Heretofore, methods of contactless testing could not be accomplished in a time period of acceptable order of magnitude.

The object of the present invention is to further develop the above described method so that short analysis times result thereby and use of the method for industrial quality control purposes is feasible.

The above object is accomplished by the present invention by a method and apparatus wherein the single pulse of the laser beam is broken up into a multiplicity of component beams whose images, simultaneously projected upon the workpiece, are combined in a field or a line by means of which the workpiece is analyzed.

The energy of an electromagnetic radiation, for example, of a laser beam, generates on the surface of the workpiece, for the duration of the irradiation, that is, for the duration of the pulse, an increase in temperature which is a function of the thermal and optical characteristics of the workpiece. A temperature compensating process occurs on the basis of thermal conductivity in the workpiece, the course of which process can be determined and evaluated in a vertical and lateral direction. The thermal compensating process occurring in the workpiece by virtue of thermal conductivity is impaired by flaws, for example, cracks, pores, poorly adhering areas of a coating layer or differences in the composition or thickness of a coating layer. These flaws can be determined on the basis of varying maximum temperatures and varying rising and falling off temperatures of the increase in temperature, resulting on the surface of the workpiece from the laser pulse. The reduction in time required to analyze test samples made possible by the present method results from the introduction of a single pulse only and the linear or surface generation of many laser beams derived from the single pulse, whose points of impact simultaneously heat up the surface of the workpiece. A larger area of the workpiece surface is consequently available for measurement. Thus, a workpiece can be analyzed in the shortest period of time, with the result that the process, for example, in the inspection of components, can be utilized in an industrial assembly-line manufacturing application. Analysis times thereby achieved are in the range of seconds because measurements and evaluation thereof can be performed in the course of a single pulse. Thus, the present procedure can be utilized even in those quality control tests where time is a critical consideration.

The individual beam component itself, whose pulse is projected against the workpiece, can be circular, rectangular, hexagonal, linear or exhibit other cross-sectional shapes. Analysis of a surface to be tested can, for example, be accomplished by a translatory displacement of the workpiece relative to the fixed aligned impact area of the beam images.

Where the analysis is performed over the surface area, the entire surface to be tested can also be tested at one time with the result that further acceleration of the inspection process can be achieved. In connection therewith, the field or impact area covered by the component beams is correspondingly measured in such a way that a single pulse suffices to cover the entire surface of the test sample which is to be heated.

With the method according to the present invention, not only is the impact area of the beams analyzed, but also the adjacent unradiated area into which heat flows until temperature compensation occurs. In the process, flaws existing not only in the irradiated areas but in those not radiated can be detected. The required distance between the component beams to be selected or the time up to temperature compensation between the individual, irradiated locations on the surface of the test sample is, among other things, a function of the workpiece's material characteristics and of the length and shape of the pulse.

Detection of the heat reflection from the workpiece surface can be performed using a thermal imaging camera or another kind of detector enabling the recording of linear or surface images. In so doing, it is possible, during the thermal penetration process and during reflection, to measure, without contact, temperatures occurring on the surface of the workpiece. The measures values yield images of a temperature pattern which, for purposes of additional evaluation, can be digitalized and read into a computer. Because the method operates in a contactless manner, it can be used under demanding industrial conditions without difficulty.

By altering the pulse length, the penetration depth of the temperature pulse and, consequently, the depth within which flaws are detected can be controlled.

The intensity of the electromagnetic radiation, for example, the intensity of the laser beam, does not, on the basis of the present method, have to be measured, such that costly optical components used to divide the beams and in measuring beam intensity can be dispensed with. Only the reflection of induced heat is measured from the surface of the workpiece. The method according to the invention, in addition to determining the location of flaws, also enables determination of the depth at which the flaws are located. Through calibration of unflawed locations and determination of the temperature gradients in the heating up and cooling down phase in comparison with areas exhibiting flaws, taking into consideration the known thermophysical characteristics of the workpiece material, the depth of flaws can be easily ascertained.

According to the present method, pulse length, pulse intensity and/or pulse shape, of the electromagnetic beam used to generate the increase in temperature on the workpiece surface and, thus, the gradients of the heating-up and cooling-down process and the maximum temperature can be varied, such that the method can be adapted easily to the material to be tested.

The apparatus for implementing the present method is characterized by its simple construction. The apparatus consists of a laser with an expansion lens directed toward the workpiece and a diaphragm with a corresponding pinhole image located in the beam path between the expansion lens and the workpiece, which breaks up the expanded beam into component beams. The apparatus has at least one infra-red sensitive detector directed at the workpiece as well as a computer used to evaluate measurements provided by the detector.

By means of the expansion lens, the laser beam generated for the duration of a pulse is expanded to the desired diameter. From the expanded beam a multiplicity of single beams is generated by means of the diaphragm. The diaphragm can, for example, contain square, round or lamellar holes. The single beams impact the workpiece to be analyzed and generate there a surface temperature pattern. The modification of the surface temperature owing to temperature compensation in a vertical and lateral direction in the workpiece can be recorded using a detector, preferably a thermal imaging camera, and, in digitalized form, fed to a computer for graphic representation and evaluation. The detector can also be located on the backside of the workpiece. A detector can also be installed respectively, on the front and backside of the workpiece, in which case the detectors can function either simultaneously or independently of each other, as the situation requires.

The apparatus can be integrated into an on-going manufacturing process by installing it for example on a conveyor path of an assembly line. Workpieces, for example, components to be tested, are guided through the working area of the apparatus and tested on a continuous basis. The apparatus can also exhibit translatory, displaceable mounting support for the workpiece, such that, for example, quality control tests are also possible on individual components which are inserted into the displaceable mounting supports.

The apparatus can also be outfitted with a cylinder lens, a reflector lens or similar optical array which focuses the beam exiting the expansion lens to a line. The linear-shaped beam is then, as described hereinbefore, again broken up into individual beams having a linear arrangement by means of a corresponding diaphragm configured as a mask.

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

Figure 1:
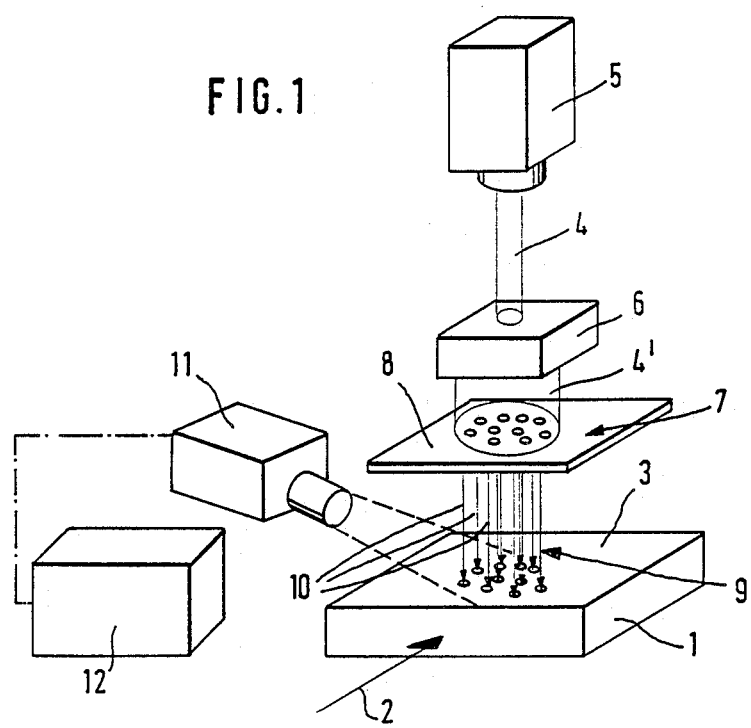
FIG. 1 is a schematic perspective view of an apparatus for the contactless testing of a workpiece.

Now turning to the drawings, there is shown in FIG. 1 an apparatus according to the present invention by means of which a workpiece or test sample 1, conveyed along an assembly line in the direction of arrow 2, can be tested for quality control purposes. The apparatus consists of a mechanism used to generate a single pulse of an electromagnetic exciting beam 4 directed toward surface 3 of workpiece 1, configured as a laser 5. Beam 4, lasting the duration of the single pulse, passes on its path toward surface 3 of workpiece 1 an expansion lens 6. After passing through expansion lens 6, the diameter of the beam is enlarged to a predetermined extent, as schematically shown at 4'. A beam separating part 7, here configured as a diaphragm 8, is located in the beam path after expansion lens 6. Diaphragm 8 can be interchangeably supported by corresponding mounting supports. The diaphragm has a predetermined pinhole image, such that expanded beam 4' is broken up into a cone 9 of component beams 10. Each component beam, upon impacting surface 3 of workpiece 1, is imaged, according to the pinhole image in diaphragm 8, as a speck of light. Each image of a component beam generates an increase in temperature on surface 3 of the workpiece during the single pulse. The increase in temperature during the cooling down phase following pulsing is measured by an infra-red sensitive detector 11 and the digitalized measurement values are fed to a computer 12 for processing and evaluation.

The infra-red sensitive detector 11 of FIG. 1, is directed toward surface 3 of workpiece 1. Of course, detector 11 can also be directed toward the backside of workpiece 1.

Figure 2:
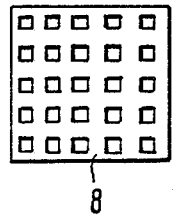
FIGS. 2 through 4 are planar views of diaphragms having varying pinhole images.
Figure 3:
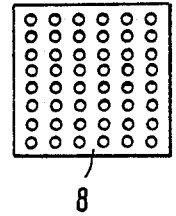
Figure 4:
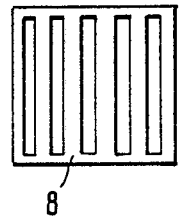

FIG. 2 shows a diaphragm 8 having square holes, FIG. 3 shows a diaphragm 8 having round holes, and in FIG. 4 lamellar holes have been formed in the diaphragm.

Figure 5:
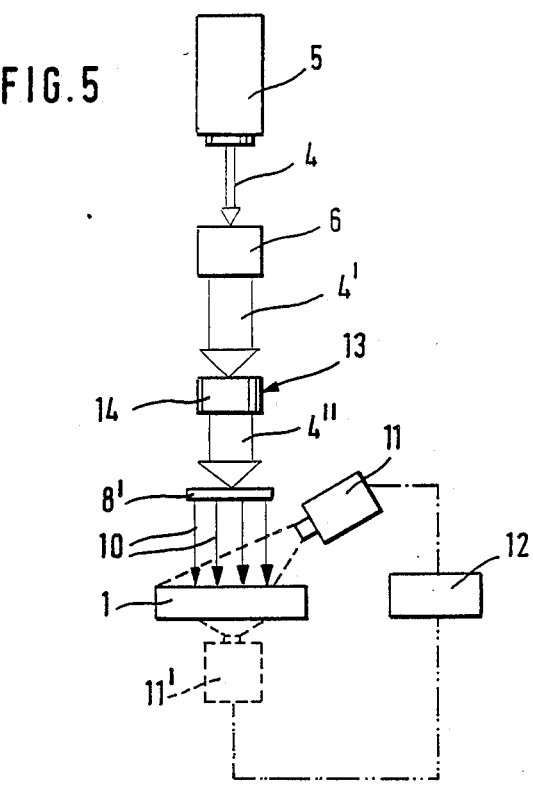
FIG. 5 is a schematic side elevational view of a second embodiment of the apparatus suitable for linear analysis of a workpiece.

FIG. 5 depicts a schematic representation of a practical execution of the device which, in contrast to the execution shown in FIG. 1 which permits surface analysis of workpiece 1, provides for linear analysis. Identical parts are again identified by identical reference numbers. In this embodiment beam 4', having exited expansion lens 6, is guided through a focusing array 13, which can, for example, be configured as a cylinder lens 14. By means of cylinder lens 14 the expanded beam is focused on a line and is designated by reference numeral 4''. Beam 4'', having been focused to a line, passes through a diaphragm 8' prior to impacting the surface of workpiece 1, whereby the focused beam can be broken up into component beams 10 by means of an apposite pinhole image in diaphragm 8'.

FIG. 5 shows that an infra-red sensitive detector 11' (shown in phantom) can be directed toward the backside of workpiece 1. Detector 11', as hereinbefore set forth, is also connected to computer 12.

Figure 6:
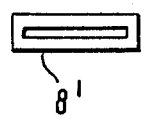
FIGS. 6 through 8 are planar views of diaphragms used in the device according to FIG. 5.
Figure 7:
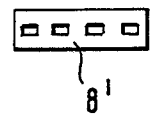
Figure 8:
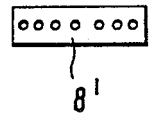

FIGS. 6 through 8 show variations of diaphragm 8' having varying pinhole images used in generating component beams which are linearly arrayed and permit linear analysis of workpiece 1.

Figure 9:
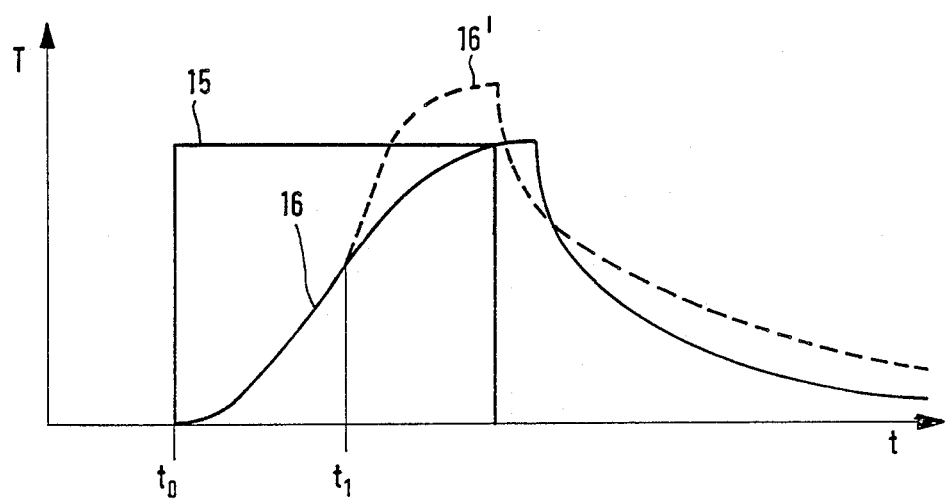
FIG. 9 is a temperature-time diagram.

In FIG. 9, a temperature(T) vs. time(t) diagram is schematically shown. Reference numeral 15 designates a rectangular pulse of a laser. The single pulse, upon impacting the surface of a workpiece, generates an increase in temperature which is exemplified by the rising flank of curve 16. The temperature pulse generated in the workpiece, that is curve 16, can be measured and evaluated using infra-red sensitive detectors. Where thermophysical characteristics such as temperature and heat conductivity, the absorption and/or emission coefficients are known, the temperature pulse 16 can also be theoretically calculated and respectively compared with measured temperature pulse values. Where there exists a pore or other flaw at a certain distance beneath the surface analyzed of the workpiece, then a deviation from measured temperature increase and cooling-off values on the surface of the component results. In the diagram of FIG. 9 it is assumed that the location of the flaw provides poorer heat conductivity. The heat of the temperature pulse is further conducted unimpeded in the time $t_0$ to $t_1$ from the surface to the location of the flaw lying below. As soon as the flaw affects the thermal conductivity process, the heating-up and cooling-down phase of temperature pulse 16 on the surface of the workpiece is modified. Through analysis of measured change in temperature of the temperature pulse on the surface, exemplified by the dashed curved 16', the depth of the flaw can be measured or, at least, estimated. Thus, for example, where the temperature conductivity of the workpiece material, where times $t_0$ to $t_1$ are known, the appurtenant site of the flaw can be determined. This can also be performed by calibration. A calibration can, for example, provide curve 16 of the temperature pulse, whereby, in which case, curve 16' of a temperature pulse, which has been measured and provides information concerning a flaw location, is measured and compared with the calibrated measurement.

While two embodiments of the present invention have been shown and described, it will be obvious that many changes and modifications may be made thereunto without departing from the spirit and scope of the invention.

What is claimed is:

1. A method for the contactless testing of the surface and inner structure of a solid workpiece, comprising:
    (a) projecting a single pulse of an electromagnetic exciting beam onto the surface of the workpiece;
    (b) breaking up said single pulse prior to contact with the surface of the workpiece into a multiplicity of individual component beams so that their images are simultaneously projected onto said workpiece combined in a field or line;
    (c) measuring the workpiece generated infra-red radiation; and
    (d) processing the measured infra-red radiation to determine the locally and temporarily induced workpiece temperature.

2. The method according to claim 1, wherein said single pulse of an electromagnetic exciting beam is a focused laser beam.

3. The method according to claim 1, wherein the length of the single pulse is varied.

4. The method according to claim 1, wherein the intensity of the single pulse is varied.

5. The method according to claim 1, wherein the length and intensity of the single pulse are varied.

6. The method according to claim 1, wherein at the unflawed locations calibration measurements are performed and compared with measurements taken at flawed locations.

7. Apparatus for the contactless testing of the surface and inner structure of a solid workpiece, comprising:
    (a) a device for generating a single pulse of an electromagnetic beam directed at the surface of the workpiece;
    (b) an expansion lens interposed in the path of said beam;
    (c) a beam separating element interposed in the path of said beam following said expansion lens, wherein said beam separating element breaks up said beam into a multiplicity of individual component beams;
    (d) at least one infra-red sensitive detector directed toward said workpiece for making measurements; and
    (e) a computer to which said detector is attached which evaluates the measurement data.

8. The apparatus according to claim 7, wherein said device for the generation of a single pulse is configured as a laser.

9. The apparatus according to claim 7, wherein said beam separating element is configured as a diaphragm.

10. The apparatus according to claim 9, wherein said diaphragm exhibits a pinhole image which corresponds to the number and distribution of component beams.

11. The apparatus according to claim 9, wherein said diaphragm is interchangeable.

12. The apparatus according to claim 7, which further includes a focusing array means disposed between said expansion lens and said beam separating element which focuses the beam on a line.

13. The apparatus according to claim 12, wherein said focusing array means is a cylindrical lens.

14. The apparatus according to claim 7, wherein said detector is a thermal imaging camera.

* * * * *